United States Patent [19]
Wang et al.

[11] Patent Number: 5,431,793
[45] Date of Patent: Jul. 11, 1995

[54] QUANTITATIVE ANALYSIS OF GLYCOSYLATED HEMOGLOBIN BY IMMUNOCAPPILLARY ELECTROPHORESIS

[75] Inventors: Hann-Ping Wang, Yorba Linda; Zara Safarian, Brea, both of Calif.

[73] Assignee: Beckman Instruments, Inc., Fullerton, Calif.

[21] Appl. No.: 283,137

[22] Filed: Jul. 29, 1994

[51] Int. Cl.$^6$ .............................................. C25B 7/00
[52] U.S. Cl. .............................. 204/182.8; 204/180.1; 204/299 R; 436/517; 436/538
[58] Field of Search ............ 204/299 R, 182.8, 180.1; 436/538, 517

[56] References Cited

U.S. PATENT DOCUMENTS

| | | | |
|---|---|---|---|
| 4,668,363 | 5/1987 | Gebott et al. | 204/182.8 |
| 4,727,036 | 2/1988 | Knowles et al. | 436/547 |
| 5,120,413 | 6/1992 | Chen et al. | 204/180.1 |
| 5,202,006 | 4/1993 | Chen | 204/180.1 |
| 5,228,960 | 7/1993 | Liu et al. | 204/182.8 |
| 5,348,633 | 9/1994 | Karger et al. | 204/180.1 |

FOREIGN PATENT DOCUMENTS 870248  6/1985  Japan.

OTHER PUBLICATIONS

CA 120:3876; CA119:23981; CA114:181696; CA117:208316; CA117:229567; CA118:251056.

Nielsen, et al., "Separation of Antibody-antigen Complexes by Capillary Zone Electrophoresis, Isolectric Focusing and High-Performance Size-Exclusion Chromatography", *Journal of Chromatography*, 539 (1991) 177-185, Elsevier Science Publishers B.V.

Saunders, W. B., Tietz, Norbert W. (editor) "Glycohemoglobins", Textbook of Clinical Chemistry, Philadelphia, 1986.

Tsieh Sun, et al., "Study of Gammopathies with Immunofixation Electrophoresis", A.J.C.P., Jul. 1979, vol. 72, No. 1, pp. 5-11.

F. Aguzzi, N. Poggi, "Immunosubtraction Electophoresis: A Simple Method for Identifying Specific Proteins Producing the Cellulose Acetate Electrophoretogram", Estratto dal, Boll. 1st. Sieroter Milanese 56, 3, 1977, pp. 212-216.

G. Merlini, et al., "Identification of Specific Plasma Proteins Determining the Agarose Gel Electrophoresis by the Immunosubtraction Technique", *J. Clin. Chem. Clin. Biochem.*, vol. 21, 1983, No. 12, pp. 841-844.

W. A. White and E. C. Attwood, "Immunofixation and Immunosubtraction on Agarose gel: An Aid in the Typing of Monoclonal Gammopathies", *Biochim. Clin.* 10, 1986, pp. 571-574.

DAKO Diagnostics Ltd., "DAKO HbA$_{1c}$" (Rev. Mar. 1993) 91-07-002.

E. Bisse & H. Wieland, "High-Performance Liquid Chromatographic Separation of Human Haemoglobins/Simultaneous Quantitation of Foetal and Glycated Haemoglobins" *Journal of Chromatography*, 434 (1988) 95-110, Elsevier Science Publishers B.V.

Guthrie, Richard M.D. et al., "A Multisite Physician's Office Laboratory Evaluation of an Immunological Method for the Measurement of HbA$_{1c}$," *Diabetes Care*, vol. 15, No. 11, Nov. 1992, pp. 1494-1498.

Goldstein, David E. et al., "Recent Advances in Glycosylated Hemoglobin Measurements," CRC *Critical Reviews in Clinical Laboratory Sciences*, vol. 21, Issue 3, pp. 187-200, 202-228.

Molteni, Sarah, Frischknecht, Hannes & Thormann, Wolfgang, "Applicant of Dynamic Capillary Isoelectric Focusing to the Analysis of Human Hemoglobin Variants," *Electrophoresis* 1994, 15, 22-30.

*Primary Examiner*—John Niebling
*Assistant Examiner*—C. Delacroix-Muirheid
*Attorney, Agent, or Firm*—William H. May; Arnold Grant; Sheldon & Mak

[57] ABSTRACT

A method useful for determining the content of a first hemoglobin in a blood sample which also contains other forms of hemoglobin is based on capillary electrophoresis. In the method, a specific binding partner to the first form of hemoglobin is added to the sample, and the sample is then subjected to capillary electrophoresis. The method is particularly suited for the determination of the percentage of Hb A$_{1c}$ in a blood sample using anti-Hb A$_{1c}$ antibody.

25 Claims, 3 Drawing Sheets

QUANTITATIVE ANALYSIS OF GLYCOSYLATED HEMOGLOBIN BY IMMUNOCAPPILLARY ELECTROPHORESIS

BACKGROUND

The present application is directed to a method of quantitative analysis of a macromolecule which is bindable by a macromolecular specific binding partner, by capillary electrophoresis.

For many purposes, it is necessary to know the amount of a target macromolecule in a sample, where the target macromolecule is similar in its chemical and biophysical properties, to another macromolecule in the sample. The similar macromolecules involved can differ in their primary structure, such as isotopes of antibodies, or can be different as the result of reactions in which only one of the two macromolecules is changed.

A clinically important example of the latter is glycosylated hemoglobin A. Human adult hemoglobin (Hb) typically consists of Hb A, Hb $A_2$, and Hb F. These forms of hemoglobin differ by virtue of their primary structure; that is, by their amino acid sequence. Normally, Hb A constitutes about 97% of the total hemoglobin present, Hb $A_2$ constitutes about 2.5% of the total, and Hb F only about 0.5%. Hb F is also referred to as fetal hemoglobin and is the normal form of hemoglobin found before birth. Shortly after birth, the normal adult form Hb A begins to predominate. In some disorders, Hb F persists. In other disorders, of which the most common is sickle cell syndrome, an abnormal hemoglobin occurs where a different amino acid sequence replaces Hb A. In sickle cell syndrome, this abnormal hemoglobin is known as Hb S.

Chromatographic analysis of Hb A has shown that it contains a number of minor hemoglobin species. Bisse and Wieland, "High Performance Liquid Chromotographic Separation of Human Hemoglobins," *J. of Chromotography*, 434 (1988) 95–110. These minor species have been designated Hb $A_{1a}$, Hb $A_{1b}$, and Hb $A_{1c}$. These species are referred to as glycosylated hemoglobins or glycohemoglobins, and are formed by condensation of the amino group of the hemoglobin with a keto moiety of a sugar. For Hb $A_{1c}$, the sugar is glucose, and the glycosylated hemoglobin is formed by the condensation of the N-terminal valine amino acid of each β-chain of the hemoglobin with glucose to form an unstable Schiff base or aldimine (also known as pre-$A_{1c}$), which then undergoes an Amadori rearrangement to form a stable ketoamine.

The formation of glycosylated hemoglobins is nonenzymatic. It occurs over the lifespan of the red cell, which is about 120 days under normal conditions. It is also proportional to the concentration of glucose in the blood. The amount of Hb $A_{1c}$ in blood is therefore related to time-averaged glucose concentration over the period of two or three months prior to the measurement. This value provides a way of assessing the control of diabetes, where the results are not affected by short-term fluctuations in plasma glucose levels. Therefore, measurement of glycohemoglobins can supplement other more traditional methods of assessing control of diabetes. For example, measurement of glycohemoglobins can be used when urine glucose records are inadequate or cannot be maintained, when blood glucose levels vary markedly throughout the day or from day to day, and for a new patient with known or suspected diabetes in whom there is no previous record of blood glucose concentration. A particular application for monitoring glycohemoglobins is during pregnancy, when close control of diabetes is especially important.

Currently available methods for the determination of glycohemoglobin include ion exchange chromatography, high-performance liquid chromatography, affinity chromatography, colorimetry, radioimmunoassay, electrophoresis, and isoelectric focusing. A comparison of these methods has been reported. Goldstein, et al., "Recent Advances in Glycosylated Hemoglobin Measurements," *C.R.C. Critical Reviews in Clinical Laboratory Sciences*, 21 (3), pp. 187–228.

Ion exchange chromatography can be carried out using resins containing weakly acidic cation exchanges or negatively charged carboxymethylcellulose resin. This procedure is time consuming and requires rigid control of temperatures of the reagents and the columns as well as the pH and the ionic strength. In practice, this means that these methods are usable only by highly skilled personnel and are not well suited to routine clinical determinations.

High performance liquid chromatography, although reliable as a reference method, also requires close control of pH and ionic strength as well as other variables.

Affinity chromatography can be used to separate nonglycosylated hemoglobin from glycosylated hemoglobin. A suitable affinity column is prepared from a gel containing immobilized m-aminophenylboronic acid on cross-linked, beaded agarose. The boronic acid reacts with the cis-diol groups of glucose bound to hemoglobin to form a reversible 5-membered ring complex, thus selectively binding the glycosylated hemoglobin to the affinity column. The nonglycosylated hemoglobin passes through the column. The glycosylated hemoglobin is then dissociated from the complex by sorbitol. Although this method is more precise, being less susceptible to variations in temperature or ionic conditions than is ion-exchange chromatography, the affinity columns must be protected from sunlight and can only be reused a limited number of times before they must be discarded.

A calorimetric method has been devised based on the observation that Hb $A_{1c}$, when subject to mild acid hydrolysis, releases 5-hydroxymethylfurfural (5-HMF). This test has proven difficult to standardize because the yield of 5-HMF from Hb $A_{1c}$ is only about 30%. In order to provide reliable results, reaction conditions must be carefully controlled. Therefore, this method is unsuitable for routine clinical analysis, particularly when rapid results are needed.

Another spectrophotometric method involves the reaction of inositol hexaphosphate (phytic acid) with hemoglobin. When phytic acid is added to a solution of hemoglobin, a shift in the absorption spectrum occurs in the visible region, as phytic acid binds to the N-terminal amino groups of the β-chains. Absorbance increases at 633 nm and decreases at 560 nm. This change only occurs for Hb A that is unglycosylated. The spectrum of glycosylated hemoglobin is not changed because the blocking effect of the glucose moiety prevents binding of phytic acid to the N-terminal amino groups of the β-chains. The change in absorbance induced by phytic acid is thus inversely proportional to the fraction of glycosylated hemoglobin. This observation can be used as the basis of a spectrophotometric assay. However, the compound 2,3-diphosphoglycerate (DPG), normally present in red cells, binds to the same region of the hemoglobin molecule as phytic acid and reduces the available sites for phytic acid. This leads to higher apparent results of glycosylated hemoglobins. Because endogenous DPG concentrations are variable and are not normally known for a given sample, the method therefore has limited applicability.

Antibody against Hb $A_{1c}$ can be prepared and used as the basis for a radioimmunoassay. Guthrie, et al., "A Multisite Physician's Office Laboratory Evaluation of an Immunological Method for the Measurement of $HbA_{io}$" *Diabetes Care*, Vol. 15, No. 11, 11/92, 1494-8. However, such a radioimmunoassay, like radioimmunoassays in general, brings with it the problems of the disposal of reagents and the short shelf life of reagents due to degradation caused by radioactive labeling, with consequent loss of specific reactivity. Thus, radioimmunoassay, though capable of accuracy, cannot generally be used for routine determinations of Hb $A_{1c}$.

Agarose gel electrophoresis is a time-consuming and tedious method.

Isoelectric focusing has also been used as a method of quantitating Hb $A_{1c}$. Although the method works well, it is cumbersome and requires accurate performance to ensure that the pH range established by the ampholytes is reproducible. Molten, et al., "Application of Dynamic Capillary Isoelectric Focusing to the Analysis of Human Hemoglobin Variants," *Electrophoresis* (1994) 15, 22–30.

In view of the shortcomings of these various methods, there is a need for an improved method that can differentiate two similar macromolecules from each other, and particularly distinguish Hb $A_{1c}$ from other forms of hemoglobin. Preferably, the method is rapid and reproducible and can be used in the clinical laboratory to aid in rapid diagnosis and to evaluate courses of treatment. Preferably, such a method reduces or eliminates the risk of operator error and does not use toxic reagents such as acrylamide solutions or radioactive reagents.

SUMMARY

We have developed a method that satisfies this need. In particular, the method can be used to determine the amount of a particular form of hemoglobin in a sample, and it is particularly useful for determining the proportion of Hb $A_{1c}$ in a blood sample that contains other forms of hemoglobin.

In this method, to a sample containing a first form of hemoglobin and at least one other form of hemoglobin, a macromolecular specific binding partner for the first form of hemoglobin is added. The specific binding partner specifically binds the first form to yield a complex, but does not bind to the other forms of hemoglobin in the sample. The sample is then subjected to capillary electrophoresis to generate an electropherogram that separates the complex from other forms of hemoglobin in the sample. From the electropherogram, it is possible to determine the proportion and/or the quantity of the first form of hemoglobin in the sample.

The first form of hemoglobin can be a glycosylated hemoglobin, such as hemoglobin $A_{1c}$ (Hb $A_{1c}$). In this case, the macromolecular specific binding partner for the first macromolecule can be an antibody that specifically binds Hb $A_{1c}$ and lacks significant binding affinity for Hb A, and other forms of hemoglobin. For the determination of the amount of Hb $A_{1c}$, a suitable detection method is detection by light absorption at 214 or 415 nm.

The method can further comprise the steps of:

(a) adding a known quantity of an internal standard compound to the sample prior to capillary electrophoresis, the internal standard compound being separable from the hemoglobin macromolecules and being detectable in the electropherogram by a signal proportional to the quantity of internal standard compound;

(b) measuring the signal produced by the internal standard compound in the electropherogram; and (c) determining the absolute concentration of the first form of hemoglobin in the sample from a standard curve of protein concentration versus the ratio of protein signal to internal standard signal.

A suitable internal standard compound is 2,4-dichlorobenzoic acid.

The amount of the complex containing the first form of hemoglobin can be determined by measuring light absorption at a wavelength at which only the hemoglobin specifically absorbs light and at which the macromolecular specific binding partner does not absorb.

If the first form of hemoglobin is Hb $A_{1c}$, and the macromolecular specific binding partner is anti-Hb $A_{1c}$ antibody, a suitable wavelength is 415 nm.

Capillary electrophoresis requires use of a buffer, and the selection of the buffer is important to the effectiveness of this method. If an incorrect buffer is used, it is not possible to obtain good separation during the capillary electrophoresis between the complex and other forms of hemoglobin present in the sample. After much experimentation, it has been determined that a suitable buffer comprises (i) water; (ii) boric acid in an amount of from about 50 to 150 mM; (iii) a borate salt in an amount of from 15 to 35 mM; (iv) a sodium or potassium salt where the anion is selected from the group consisting of sulfate, chloride, fluoride, iodide, and bromide ions, the amount of sodium or potassium salt being from 50 to 100 mM; and (v) sufficient base compound that the buffer has a pH of from 8 to 10.

It has been determined that this method can effectively differentiate Hb $A_{1c}$ from other forms of hemoglobin in a blood sample, and can be used to quantitate the percentages of Hb $A_{1c}$ in the sample. Moreover, the method is rapidly reproducible, and can be used in a clinical laboratory to aid in rapid diagnosis and evaluate courses of treatment. Further, the method provides no risk to the operator that can be associated with use of toxic reagents.

DRAWINGS

These and other features, aspects, and advantages of the present invention will become better understood with reference to the following description, appended claims, and accompanying drawing where:

DESCRIPTION

We have developed a method for differentiating two macromolecules in a sample and determining the content of at least one of the macromolecules in the sample. This method utilizes capillary electrophoresis and a macromolecular specific binding partner that can bind to one of the macromolecules and not the other. The macromolecules must have molecular properties such that the binding of the macromolecular specific binding partner to the macromolecule to which it binds forms a complex that can be differentiated on capillary electrophoresis from the macromolecule to which the macromolecular specific binding partner does not bind. Typically, the macromolecules themselves are not adequately resolved by capillary electrophoresis in the absence of binding to the specific binding partner. This means that, if the macromolecular specific binding partner were not used, substantially only a single peak would be obtained on capillary electrophoresis, the area of which would represent the quantity of both the first and second macromolecules.

I. METHOD FOR DIFFERENTIATING AND DETERMINING MACROMOLECULE CONTENT

In a preferred version of the present invention, (i) a complex of the macromolecular specific binding partner and the corresponding macromolecules and (ii) the other macromolecule in a sample are detected in capillary electropherograms. In general, this method comprises:

(1) reacting a sample with a macromolecular specific binding partner that specifically binds a first macromolecule to form a complex between the macromolecular specific binding partner and the first macromolecule, the quantity of macromolecular specific binding partner being sufficient to cause substantially all of the first macromolecule to be present in the complex;

(2) subjecting the sample, subsequent to formation of the complex between the first macromolecule and the macromolecular specific binding partner, to capillary electrophoresis to generate a first electropherogram that separates: (i) macromolecular specific binding partner unbound to the first macromolecule; (ii) the complex of the macromolecular specific binding partner and the first macromolecule; and (iii) a second macromolecule that is unbound to the macromolecular specific binding partner; and (3) determining the proportion of the first macromolecule in the sample, and optionally the second macromolecule, from the electropherogram.

Figure 1:
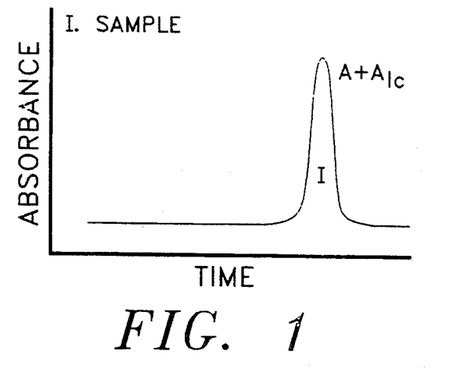
FIG. 1 is an idealized electropherogram resulting from electrophoresis of a sample containing hemoglobin that has not been reacted with macromolecular specific binding partner.

With reference to FIG. 1, the area, x, under the peak represents the two unseparated macromolecules A and $A_{1c}$, and the area under the peak representing only the second macromolecule A+ (the macromolecule that does not bind to the macromolecular specific binding partner) is y. Thus, the quantity of the first macromolecule $A_{1c}$ (i.e., the one that binds to the macromolecular specific binding partner) is x-y.

Figure 2:
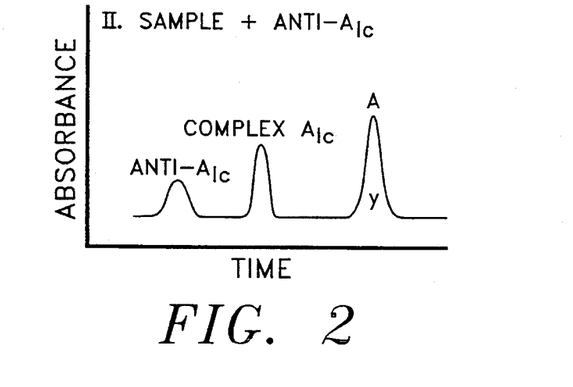
FIG. 2 is an idealized electropherogram resulting from electrophoresis of the sample, after it has been reacted with macromolecular specific binding partner, in which the three peaks are (i) the macromolecular specific binding partner, (ii) the complex of the macromolecular specific binding partner and a first form of hemoglobin, and (iii) another form of hemoglobin.
Figure 3:
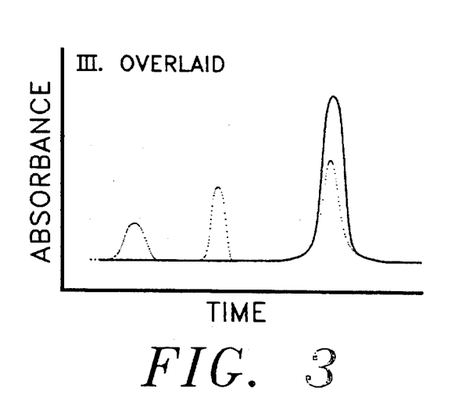
FIG. 3 shows the superimposition of the idealized electropherograms of FIGS. 1 and 2.

In FIG. 2 the three peaks are the macromolecular specific binding partner (Anti-$A_{1c}$), the complex of the macromolecular specific binding partner and the first macromolecule (complex $A_{1c}$), and the second macromolecule (A). FIG. 1 shows the electropherogram of the sample before adding the binding partner, in which the only peak includes both the first and the second macromolecule. FIG. 3 shows the electropherograms of FIG. 1 and FIG. 2 superimposed.

Typically, the first macromolecule, the second macromolecule, and the complex are detected after capillary electrophoresis by light absorption spectroscopy in the ultraviolet or visible regions of the spectrum. The wavelength chosen depends on the properties of the macromolecules. When the first and second macromolecules are proteins, a preferred wavelength for detection is 214 nm. In this context, the term "proteins" includes conjugated proteins such as myoglobin, hemoglobin and other proteins conjugated with a prosthetic group, as well as glycoproteins. The absorption at 214 nm is substantially dependent on the peptide bond and is not significantly affected by the presence of other groups.

It is preferred to use a quantity of the macromolecular specific binding partner that is sufficient to bind substantially all of the first macromolecule present in the sample.

Typically, the macromolecular specific binding partner and the first and second macromolecules are within about an order of magnitude in molecular weight. For example, hemoglobins have a molecular weight of about 65,000.

When the macromolecular specific binding partner is an antibody, it is preferred to use a quantity of the antibody sufficiently large so that only one of the two antigen binding sites on the antibody need be occupied. Because there is no need in this method to form a precipitating complex or lattice of the macromolecular specific binding partner and the first macromolecule, an excess of antibody does no harm.

It is also possible to use univalent antigen binding fragments such as Fab or F(ab') fragments. Divalent F(ab')$_2$ fragments can also be used.

The reaction between the macromolecule specific binding partner and the first and second macromolecules to bind the first macromolecule to the macromolecular specific binding partner, is performed under conditions that allow for the formation and measurement of the complex between the first macromolecule and the macromolecular specific binding partner. The reaction can be performed at temperatures ranging from about 10° C. to about 37° C. In some cases, slightly higher temperatures can be used. The use of a higher temperature generally accelerates the reaction, while the use of a lower temperature can prevent degradation of sensitive components. Typically, the reaction is performed at ambient temperature. Typically, the reaction is performed at a pH of from about 5.5 to about 8.5, more typically from about 6 to about 8. Preferably, the reaction is performed at a pH of from about 7 to about 7.5. Preferably, a buffer is used in the reaction mixture to adjust the pH and keep it constant. Many suitable buffers are known in the art and need not be described further here, but commonly-used buffers include phosphate and Tris. The particular buffer chosen can depend on the nature of the macromolecular specific binding partner and the first and second macromolecules, as well as the particular pH range desired and the presence of acidic or alkaline components in the sample.

The reaction mixture can also contain other components, such as antioxidants, preservatives, emulsifiers, or detergents, depending on the nature of the sample. In some cases, a detergent such as Tween or Triton can be included at a low concentration to prevent non-specific aggregation, particularly of hydrophobic components. Other components, such as inert proteins, can also be added as needed.

The time for reaction is typically from 30 seconds to about 30 minutes, most typically from about 1 to 5 minutes. The time for reaction chosen is sufficient to allow substantially complete binding of the first macromolecule to the macromolecular specific binding partner. In some cases, it can be desirable to agitate the reaction to accelerate the binding. However, such agitation should avoid denaturation of proteins or other active components.

The method of the present invention can determine the relative proportions of any two similar macromolecules as long as a macromolecular specific binding partner exists that can differentiate between the molecules. The present invention is particularly suitable for hemoglobins, including glycosylated hemoglobins, polysaccharides, and antibodies.

One particularly suitable use of the method of the present invention is in the determination of the proportion of Hb $A_{1c}$ to Hb A. For the determination of the relative proportion of these two forms of hemoglobin, antibodies that specifically bind Hb $A_{1c}$ and substantially lack binding to Hb A are available. One such antibody, and in particular a monoclonal antibody, has been prepared in mice. It is commercially available from Dako Corp. of Copenhagen, Denmark. Although a monospecific polyclonal antibody can be used for the reaction, a monoclonal antibody is preferred.

Immunoglobulins is another system in which the method of the present invention can be used. For example, the method can be used to quantitate the fraction of each of the four subclasses of human immunoglobulin G, designated IgG1, IgG2, IgG3, and IgG4. These molecules have substantial homology in their amino acid sequences, about 95%. However, antibodies can be prepared in other organisms, such as rabbits, that recognize each of the four subclasses and not any of the other subclasses. A suitable antibody for igG is described in copending U.S. patent application Ser. No. 08/186,347, filed on Jan. 25, 1994, entitled "A Capillary Electrophoresis Immunosubtraction for Classification and Typing of Non-Proteins" (Attorney Docket No. 0390-1129), which is incorporated herein by reference. Thus, for example, an antibody to IgG1 can be used as the macromolecular specific binding partner in order to determine the proportion of IgG1 in the total population of IgG. Similarly, immunoglobulin A has two subclasses, IgA1 and IgA2, that can be distinguished by the use of specific anti-subclass antibodies.

Another application of the method of the present invention is in the quantitation and differentiation of polysaccharide molecules. These molecules are also antigenic, and antibodies can be prepared that can recognize one polysaccharide and yet do not bind with another polysaccharide of similar although different structure. Examples of such polysaccharides include capsular antigens of enterobacteria such as *Salmonella*.

The present invention can use an internal standard to calculate the absolute concentration of the first macromolecule in the sample. This is carried out by adding a known quantity of an internal standard compound to the sample. The internal standard compound produces a signal in relation to its concentration and is capable of electrophoretic separation from the first and second macromolecules, the macromolecular specific binding partner, and any complex of the first macromolecule and the macromolecular specific binding partner. The signal produced by the internal standard compound is then measured and compared to the signal produced by the second macromolecule to determine a ratio of internal standard signal to the signal produced by the second macromolecule. The absolute concentration of the second macromolecule in the sample is then determined from a standard curve of protein concentration versus the ratio of protein signal to internal standard signal.

The absolute concentration of either the first or second macromolecules can also be established by running an electropherogram containing (i) a known quantity of the second macromolecule, or (ii) a known quantity of the first macromolecule plus a quantity of the macromolecular specific binding partner sufficient to bind all of the standard concentration of the first macromolecule, and then comparing the area under the peak of the appropriate signal generated. This allows determination of the absolute quantity of the first or second macromolecule in the initial test sample by using the ratio of the signal in this electropherogram to the ratio of the signal in the first electropherogram for either the second macromolecule or the complex of the first macromolecule and the macromolecular specific binding partner. However, it is generally preferable to use an internal standard compound, as it avoids the necessity of running another electropherogram.

When the first and second macromolecules are proteins and the macromolecular specific binding partner is an anti-protein antibody, and detection is performed at 214 nm, typically the internal standard compound is a benzoic acid substituted with at least one halogen. Preferably, the internal standard compound is a dichlorobenzoic acid, a monochlorobenzoic acid, or a trichlorobenzoic acid. Most preferably, the internal standard compound is a dichlorobenzoic acid. A highly preferred internal standard compound is 2,4-dichlorobenzoic acid. If the internal standard compound is a trichlorobenzoic acid, a highly preferred internal standard is 2,4,6-trichlorobenzoic acid.

Depending on the wavelength of light used to analyze the sample, the binding partner may not be detected. In general, this means that the detection is performed by light absorption in the ultraviolet or visible regions of the spectrum at a wavelength or wavelengths at which the macromolecular specific binding partner does not exhibit significant absorbance.

Figure 4:
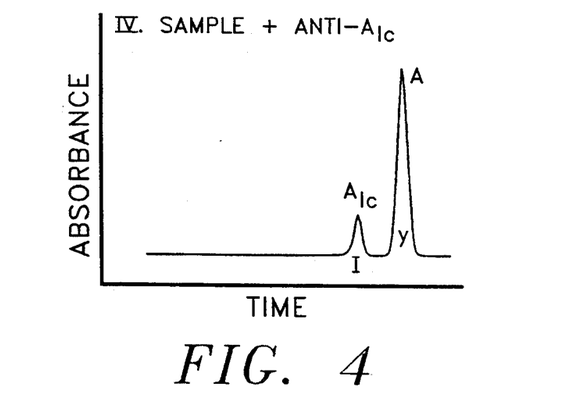
FIG. 4 is an idealized electropherogram showing both (i) the complex of the first macromolecule and the macromolecular specific binding partner and (ii) the unbound second macromolecule, and in which the signal detected derives only from the first and second macromolecules and not from the specific binding partner.

When the first macromolecule is a glycosylated hemoglobin such as Hb $A_{1c}$ and the second macromolecule is Hb A, and the specific binding partner is antibody to Hb $A_{1c}$, preferably detection is performed by monitoring light absorption at 415 nm. This is a wavelength at which the antibody does not absorb but at which the hemoglobins do absorb, due to their heme moieties. Accordingly, the resulting electropherogram depicts both the first macromolecule, in this case the Hb $A_{1c}$, bound to the antibody in the complex as one absorbance peak, and depicts the second macromolecule, Hb A, unbound as another absorbance peak. The areas under the absorbance peaks are due only to the hemoglobins themselves, and not to the antibody in the complex, because only the hemoglobins absorb light at 415 nm. Such an electropherogram is shown in FIG. 4. In this embodiment of the invention, a subtractive technique is not necessary, and the ratio of glycosylated hemoglobin (x-y) to nonglycosylated hemoglobin (y) can be obtained directly by comparing the areas under the two peaks.

II. GENERAL PRINCIPLES OF MACROMOLECULE DETECTION BY CAPILLARY ELECTROPHORESIS

A. Optical Detection of Macromolecules

A number of detectable signals produced by macromolecules such as proteins can be used for their detection subsequent to capillary electrophoresis. These signals include, but are not necessarily limited to, those resulting from absorption of light in the ultraviolet or visible portions of the spectrum, those resulting from fluorescence and/or chemiluminescence, those resulting from refractive index changes, and those resulting from optical rotation such as circular dichroism and optical rotatory dispersion. Typically, absorption of light in the ultraviolet or visible portions of the spectrum is used. Other types of signals, such as those resulting from electrochemical reactions, can also be used.

Most macromolecules are detectable by their absorption of ultraviolet or visible radiation. This absorption is a consequence of the electronic structure of the molecule and yields an absorption spectrum that is specific for each molecule. At any wavelength in dilute solution, the relationship between the intensity of radiation transmitted to the intensity of the incident radiation is governed by the Beer-Lambert Law: $I = I_o \times 10^{\epsilon l c}$ where $I_o$ is the intensity of the incident radiation and $I$ is the intensity of the radiation transmitted through a cell of thickness 1 cm, containing a solution of concentration c moles/liter. The quantity $\epsilon$ is the extinction coefficient, with the units liter mole$^{-1}$ cm$^{-1}$.

Thus, from a determination of the transmitted radiation and the known intensity of the incident radiation, the concentration of any solute can be determined if the extinction coefficient is known at a particular wavelength, as long as the path length is also known. In the typical apparatus for measurement of ultraviolet absorption, which includes the capillary electrophoresis apparatus adapted to the method of the present invention, the thickness of the cell is known from the construction of the cell.

In practice, as discussed below, because the cell thickness is constant, all that is needed is a ratio of the ultraviolet or visible absorption for a particular peak as compared with the absorption at the same wavelength for an internal standard. This ratio is then used in connection with a standard curve of protein concentration versus the ratio of protein ultraviolet absorption to internal standard absorption.

If a sample contains more than one protein species and the protein species are separated from each other, such as by capillary electrophoresis, the total protein concentration in the sample can be determined by integrating the signal obtained from each separated species and then using the total integrated signal obtained from the integration to extrapolate total protein concentration from the standard curve. This yields the total protein concentration in the sample.

1. Detection of Proteins

It is preferred to detect proteins at a wavelength of 214 nm, in the relatively far ultraviolet. At this wavelength, the peptide bonds of the protein molecules absorb. At this wavelength, the extinction coefficient of various proteins are virtually equal; i.e., there is little dependence of the extinction coefficient on any of the following variables: the amino acid composition of the protein, the primary structure of the protein, or the secondary, tertiary, or quaternary structure of the protein. Thus, absorption at this wavelength is an excellent measure of total protein concentration as well as being suitable for the determination of the concentration of an individual protein that is separated from other proteins originally present in a mixture. This is what occurs during capillary electrophoresis, as discussed below.

Alternatively, proteins can be detected by their ultraviolet absorption at a range of wavelengths centered around 280 nm. Absorption in this range of wavelengths is predominantly due to aromatic amino acid residues, particularly tyrosine and tryptophan, and, to a lesser extent, phenylalanine. Accordingly, absorption in this range of wavelengths varies with the amino acid composition of the protein. It also varies with the secondary, tertiary, and quaternary structure of the protein because absorption at this range of wavelengths depends to a substantial degree on the interaction of the residues involved with the solvent. Although it is generally preferred to work at 214 nm, in some cases, it can be desirable to work at longer wavelengths.

As another alternative, a number of proteins possess prosthetic groups that absorb light at particular wavelengths. For example, the heme group of hemoproteins such as hemoglobin and myoglobin absorbs light at 415 nm and can be detected by monitoring absorption at that wavelength. Other proteins have prosthetic groups such as reduced or oxidized flavin adenine dinucleotide, and can be detected based on the absorbance of these prosthetic groups.

2. Detection of Nucleic Acids

Nucleic acids have strong ultraviolet absorptions in the range of 260 nm. This absorption is due to the heterocyclic rings in the nucleotide bases adenine, cytosine, guanine, and thymine (or uracil for RNA). For nucleic acids, the various bases have different absorption maxima and absorption intensity, so the molar absorption intensity varies to a certain extent with base composition. The absorption also varies with the secondary structure of the nucleic acid. Double-stranded nucleic acids such as native DNA have approximately a 30% lower ultraviolet absorption per mole of bases than do single-stranded nucleic acids. This effect is known as hypochromism. However, if the composition and strandedness of the nucleic acid are known, its concentration can be readily determined from the intensity of ultraviolet absorption.

B. Capillary Electrophoresis

In the present invention capillary electrophoresis is used.

1. Basic Principles of Capillary Electrophoresis

Capillary zone electrophoresis (CZE) or capillary electrophoresis, is a technique that employs narrow-bore (10–200 μm inside diameter) capillaries to perform high efficiency separations of both large and small molecules. This separation is facilitated by the use of high voltages, typically 1000 to 30,000 volts, which can generate electroendoosmotic and electrophoretic flow of buffer solutions and ionic species, respectively, within the capillary. The properties of the separation and the ensuing electropherogram have characteristics resembling a cross between traditional polyacrylamide gel electrophoresis (PAGE) and modern high performance liquid chromatography (HPLC).

The force for moving fluid between the sample input and the sample output of the capillary tube is provided by establishing an appropriate voltage between the sample input and the sample output, generating electrophoretic and electroendoosmotic forces as discussed above.

Electroosmosis is a consequence of the surface charge on the wall of the capillary. The fused silica capillaries that are typically used for separations have ionizable silanol groups in contact with the buffer contained within the capillary. The pI of fused silica is about 1.5. The degree of ionization is controlled mainly by the pH of the buffer. Most buffers in which the pH is greater than 1.5 can ionize the capillary wall. The negatively-charged wall attracts positively charged ions from the buffer, creating an electrical double layer. When a voltage is applied across the capillary, cations in the diffuse portion of the double layer migrate in the direction of the cathode carrying water with them. The result is an electroosmotic flow (EOF) of buffer solution in the direction of the negative electrode. In the meantime, the negatively charged analytes, such as proteins, peptides, or other species, in the buffer solution can move against the EOF by electrophoretic migration towards the positive electrodes. Despite the electrophoretic migration of the analytes towards the positive electrode (anode), EOF overwhelms the electrophoretic migration of the analytes, and the analytes migrate toward the negative electrode (cathode). Electrophoretic migration is dependent upon the charge-mass ratio of each molecule, e.g., protein, to be separated. Each molecule possesses a specific charge-mass ratio depending upon its size and amino acid composition and thus migrates with a different speed. In the capillary electrophoresis apparatus, the detection window is arranged in relationship to the point at which the sample enters the electrophoretic field so that the sample is carried to the detection window by EOF. Accordingly, the faster the movement against EOF, the slower a particular protein passes the detection window. This is analogous to a group of very lazy rowboaters who are rowing against the current but are carried downstream faster than they can row. An observer at a point some distance downstream would first be reached by the rower who is rowing the slowest, because his net motion would be the closest to that of the current. The rower who was rowing the most vigorously would in fact arrive last at the observer. Thus, proteins with a high degree of negative charge caused by a high proportion of the negatively charged amino acid residues aspartate and glutamate would arrive at the detection window most slowly. Accordingly, what is measured in capillary electrophoresis is the absorption of the sample passing the detection window as a function of time. This curve yields a series of peaks corresponding to particular protein species. Integrating the area under the peak can therefore be used to quantitate the amount of a particular protein species, and integrating the total area under all peaks of the electropherogram can be used to quantitate the total protein content of the sample.

2. Apparatus for Performing Capillary Electrophoresis

The process of capillary electrophoresis can be performed in any apparatus in which the suitable electrophoretic forces can be generated and in which the peaks resulting can be detected. Typically, the capillary electrophoresis system involves a quartz or fused silica capillary tube of circular cross-section and cylindrical outline, equipped with an ultraviolet emitter and monochromator to select the desired wavelength, as well as a photodetector to detect the ultraviolet light that has passed through the sample. Typical dimensions of the capillary tube are 25 $\mu$m inner diameter $\times$ 27 cm total length. A suitable capillary tube is that produced by Polymicro Technologies, Phoenix, Ariz. The outer surface of the capillary can be coated with polyimide to protect the capillary from breakage. The optics module and detector can include a UV light source (deuterium lamp) and a 214 nanometer filter in a rotating wheel, as well as a detector that aligns with the aperture of the window. The window can be located at 6.5 cm from the tube outlet. A suitable apparatus for detection of proteins based on ultraviolet absorbance at 214 nm is the Beckman Instruments P/ACE CE system (Beckman Instruments, Fullerton, Calif.). This system is computer-controlled and can be used with suitable software, such as the Beckman "System Gold" software, and an IBM-compatible personal computer such as an IBM PS/2. Other suitable capillary electrophoresis apparatus can also be used.

Although the detected signal has been described for particular wavelengths, in particular 214 nanometers for peptide bonds, it is apparent that the electrophoresis system could operate at many different wavelengths. Another example of a suitable wavelength is 415 nm for the detection of hemoproteins such as hemoglobin. Signals at multiple discrete wavelengths can be applied to one or more detection paths applied to the tube.

Although the electrophoresis system used for the methods of the present invention has been described with reference to a single capillary electrophoresis unit, it is clear that multiple systems can be used in series or tandem to provide for a continuous monitoring process, such as a time series of protein concentration in a sample. This can be useful when monitoring the development of clinical conditions.

In other situations, it is possible to have multiple input windows and output windows arranged angularly around the central axis of a capillary tube at selective angles. In different situations, input light of different selected wavelengths can be input into the capillary tube through selected input windows about the axis. Different output windows would then receive the light with the pertinent information about the sample in the tube.

A suitable apparatus for practicing the present invention is described in U.S. patent application Ser. No. 07/916,307, filed on Jul. 17, 1992, entitled "Method and Apparatus for Displaying Capillary Electrophoresis Data," (Attorney Docket No. 10355/390-1077 which is incorporated herein by reference.

It has been determined that selection of the appropriate buffer for the capillary electrophoresis is critical for the differentiation of Hb $A_{1c}$ bound to a monoclonal antibody from Hb A, without breaking the bond between the antibody for Hb $A_{1c}$ and Hb $A_{1c}$. A buffer that meets these requirements comprises (i) water, (ii) boric acid, (iii) borate salt, (iv) a sodium or potassium salt, wherein the anion is selected from the group consisting of sulfate, chloride, fluoride, iodide, and bromide ions, and (v) sufficient base, preferably sodium hydroxide, that the buffer has a pH of from 8 to 10.

The boric acid is present in an amount of from 50 to 150 mM, and preferably from 75 to 125 mM. The borate salt, which is preferably borax, is present in an amount of from 15 to 35 mM, and preferably from 20 to 30 mM.

Preferably the sodium or potassium salt is sodium chloride. The sodium or potassium salt is present in an amount of from 50 to 100 mM, and preferably from 70 to 80 mM.

The optimum buffer has been determined to contain boric acid in an amount of about 100 mM, borax in an amount of about 20 mM, sodium chloride in an amount of about 75 mM, and sufficient sodium hydroxide so that the buffer has a pH of about 8.8.

The invention is illustrated by the following Examples. The Examples are for illustrative purposes only and are not intended to limit the invention.

EXAMPLES

Example 1

Determination of Hb $A_{1c}$

The proportion of hemoglobin $A_{1c}$ (Hb $A_{1c}$) to hemoglobin A (Hb A) was determined using anti-Hb $A_{1c}$ antibody and detection at 214 nm or 415 nm after capillary electrophoresis.

A blood sample was obtained from a diabetic patient. The sample contained about 10% Hb $A_{1c}$ as determined by the Bio-Rad® ion exchange column chromatographic method. Packed red cells were collected by spontaneous settling of the sample followed by a brief centrifugation. Hemoglobin was obtained by hemolyzing the unwashed packed red cells with Beckman Diatrac hemolyzing reagent at a volume to volume ratio of 1:3.5. After a brief centrifugation to remove any cell debris, the lysed red cells were further diluted with 5.5-fold the packed red cell volume of distilled water, and dialyzed against Beckman ICS buffer (pH 6.8).

The sample was reacted with anti-Hb $A_{1c}$ antibody (Dako Corporation, protein concentration 2.38 mg/ml in PBS (phosphate buffer saline) plus $NAN_3$, with a final diluted volume antibody equal to the volume of the blood sample being used. The reaction mixture containing the antibody and the hemoglobin was allowed to react for 5 to 30 minutes at 25° C. Subsequent to the reaction, the sample was subjected to capillary electrophoresis by the following procedure:

Apparatus

A Beckman P/ACE 2000 CE system was used with Beckman CCE software, a modification of "System Gold", which is controlled by an IBM PS/2 PC. Electrophoresis was performed in an untreated fused silica capillary tube. The outer surface of the capillary was coated with polyimide to protect the capillary from breakage (Polymicro Technologies, Inc., Phoenix, Ariz.). The optics module and detector included a UV light source (deuterium lamp) and a 214 nanometer filter in a rotating wheel, as well as a detector that aligned with the aperture of the window. The window was located at 6.5 cm from the tube outlet.

Capillary Electrophoresis Reagents

Running buffer was prepared as follows: 6–18 g of boric acid, 4.38 g. of sodium chloride, and 9.5 g. of salt were dissolved into 800 ml of deionized water. A pH meter was calibrated with two standard pH solutions at pH 7.0 and 10.0, and the boric acid solution was then adjusted to a pH of 8.46 with 1N NaOH. The boric acid solution was then adjusted to a final volume of 1000 ml using volumetric apparatus and filtered through a 0.22 $\mu$m membrane (Corning, Corning, N.Y., Filter Catalog Number 25952) and stored at room temperature in a glass bottle.

Rinse solution A was 1N NaOH. Rinse solution B was deionized water.

Procedure for Capillary Electrophoresis

The sample was diluted to a final total volume of 300 $\mu$l with one part of sample being diluted with 9 parts of sample diluent (PBS). The vial was then placed on the sample tray of the electrophoresis apparatus. The parameters for electrophoresis were set as follows: The capillary was 25 $\mu$m × 27 cm, with a separation length of 20 cm. The wavelength for measurements was 214 nm and 415 nm. The temperature was 24° C. The injection mode was pressure injection for 10 seconds. The separation voltage was 5 kilovolts (185 v/cm). The separation time was 8 minutes. The current was 12.8 $\mu$A.

The operating sequence was set as follows: The column was rinsed with running buffer for 1.5 minutes. The column was equilibrated with running buffer for 0.5 minutes. Pressure injection was performed for ten seconds as indicated, and the separation was performed at 5 kilovolts voltage for 8 minutes. The column was then rinsed with rinse solution A for 1 minute, and then with rinse solution B for 1 minute.

Column maintenance was as follows: At the beginning of each day, the column was rinsed with rinse solution A for 1 minute, rinse solution B for 5 minutes, and running buffer for 15 minutes. At the end of each day, the column was rinsed with rinse solution A for 1 minute and rinse solution B for 5 minutes.

For data analysis, the CCE software was used to adjust the baseline. The "delimit" integrator function was then used to calculate the relative area under the peaks and the required ratios of the peak areas.

Figure 5:
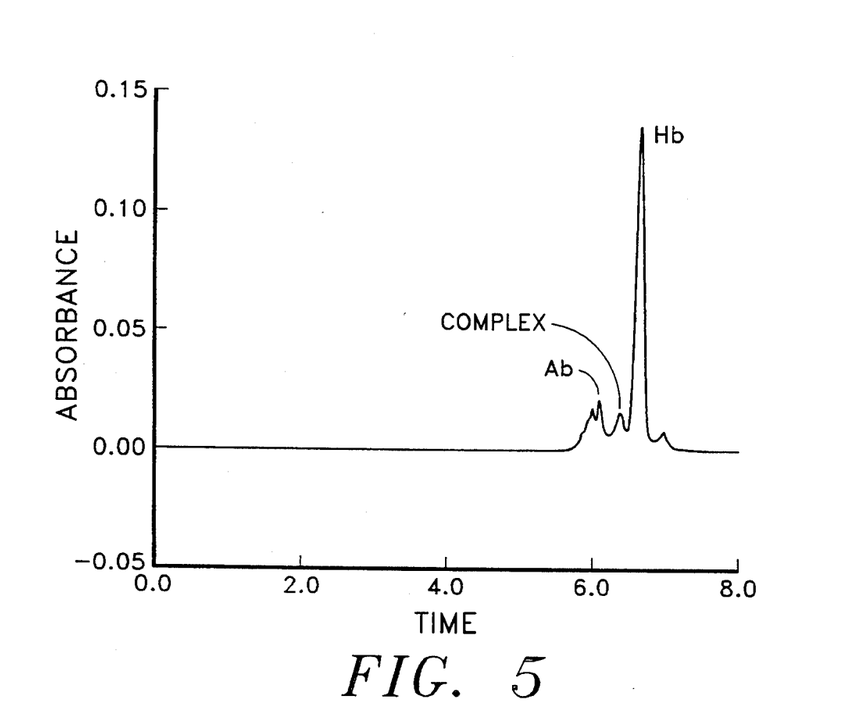
FIGS. 5–8 provide electropherograms resulting from application of the method of the present invention to a blood sample from diabetic patients.
Figure 6:
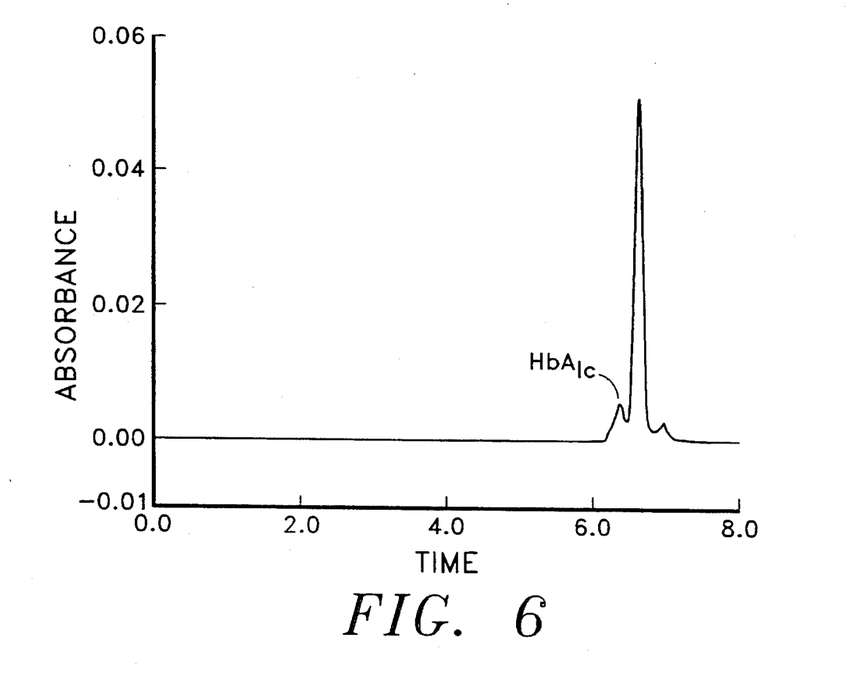

FIG. 5 is an electropherogram at 214 nm, and FIG. 6 is an electropherogram at 415 nm. The detection at 214 nm monitors the protein moiety of the analytes. Detection at 415 monitors the heme moiety of the analyte. In FIG. 5 the Hb $A_{1c}$ is indicated by an arrow. Integration of the peak areas in FIG. 5 reveals that the Hb $A_{1c}$ peak represents about 10% of the total hemoglobin, indicating that the method of the present invention and the Bio-Rad ion exchange method produce equivalent results.

Example 2

This example is the same as Example 1, except that sample was obtained from a different diabetic patient, and a different running buffer was used. The running buffer contained 150 mm of boric acid and had a pH of 10.0.

Figure 7:
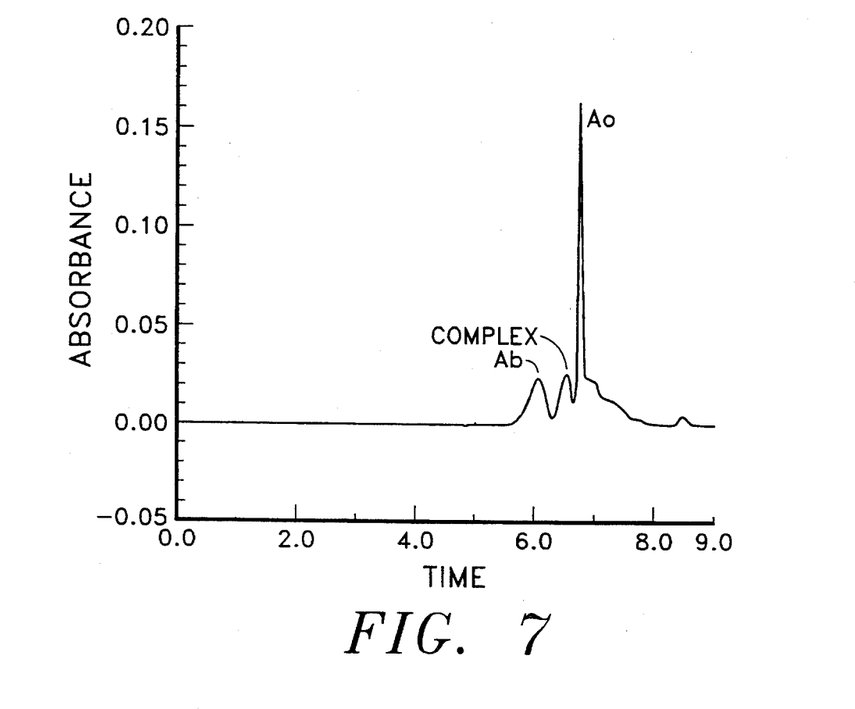
Figure 8:
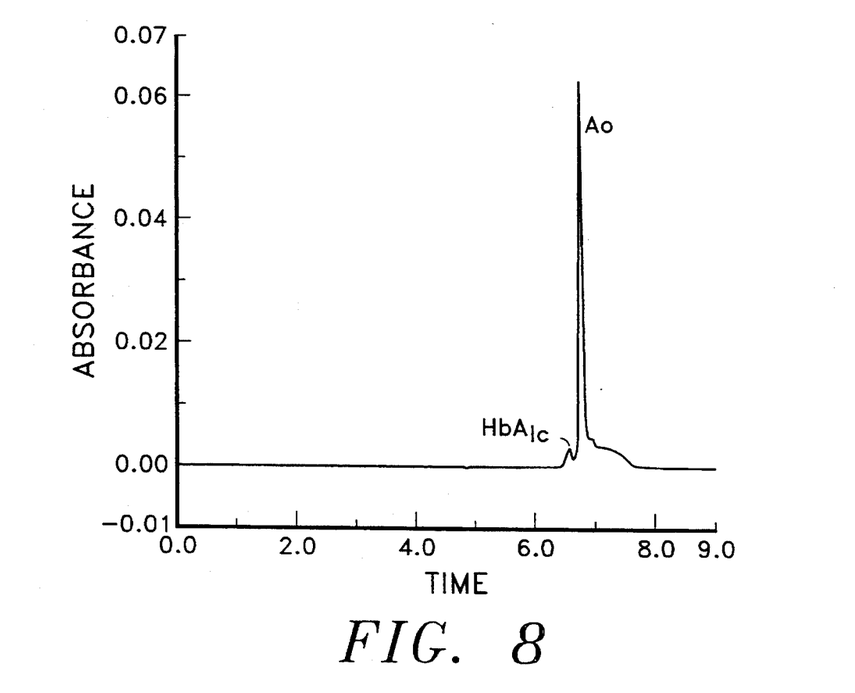

FIG. 7 is an electropherogram at 214 mm, and FIG. 8 is an electropherogram at 415 mm. Integration of the peak areas in FIG. 7 reveals that the Hb $A_{1c}$ at peak represents about 13 percent of the total hemoglobin.

Integration of the peak areas in FIG. 8 reveals that the Hb $A_{1c}$ peak represents about 12 percent of the total hemoglobin. Thus, the two electropherograms are in close agreement.

ADVANTAGES OF THE INVENTION

The method of the present invention can rapidly differentiate two similar macromolecules from each other when only one of the macromolecules is bindable by a specific binding partner, in order to determine the content of at least one macromolecule in a sample. This method is readily applicable to the determination of the Hb $A_{1c}$ and A percentages in a blood sample. The method is rapid and reproducible and, when performed on commercially-available automated capillary electrophoresis equipment, reduces or eliminates the risk of operator error. The use of toxic or radioactive reagents is also eliminated. The macromolecular specific binding partner can be a suitable antibody. Thus, the method does not depend on a specific chemical reaction, such as covalent modification, that is limited to one or a few classes of molecules.

Although the present invention has been described in considerable detail with reference to certain preferred versions thereof, other versions are possible. Therefore, the scope of the appended claims should not be limited to the description of the preferred versions contained herein.

What is claimed is:

1. A method for determining the content of a first form of hemoglobin in a sample that also contains at least one other form of hemoglobin, the method comprising the steps of:
   (a) adding to a sample containing a first form of hemoglobin and at least one other form of hemoglobin, a macromolecular specific binding partner for the first form of hemoglobin, the specific binding partner specifically binding the first form to yield a complex and not binding to the other forms of hemoglobin in the sample;
   (b) subjecting the sample, after step (a), to capillary electrophoresis to generate an electropherogram that separates the complex from the other forms of hemoglobin in the sample; and
   (c) determining the content of the first form of hemoglobin in the sample from the electropherogram.

2. The method of claim 1 wherein the first form of hemoglobin is a glycosylated hemoglobin.

3. The method of claim 2 wherein the glycosylated hemoglobin is hemoglobin $A_{1c}$.

4. The method of claim 3 wherein the macromolecular specific binding partner is an antibody that specifically binds Hb $A_{1c}$ and lacks significant binding affinity for Hb A and other hemoglobin variants.

5. The method of claim 4 wherein step (c) comprises determining the ratio of Hb $A_{1c}$ to Hb in the sample.

6. The method of claim 4 wherein the step of determining quantity comprises measuring light absorption at 214 nm in the electropherogram.

7. The method of claim 1 further comprising the steps of:
   (d) adding a known quantity of an internal standard compound to the sample prior to capillary electrophoresis, the internal standard compound being separable from the hemoglobin and being detectable in the electropherogram by a signal proportional to the quantity of internal standard compound;
   (e) measuring the signal produced by the internal standard compound in the electropherogram; and
   (f) determining the absolute concentration of the first form of hemoglobin in the sample from a standard curve of protein concentration versus the ratio of protein signal to internal standard signal.

8. The method of claim 7 wherein the first form of hemoglobin is Hb $A_{1c}$.

9. The method of claim 7 wherein the internal standard compound is 2,4-dichlorobenzoic acid.

10. A method for determining the Hb $A_{1c}$ content of a sample that also contains at least one other form of hemoglobin, the method comprising the steps of:
    (a) adding to a sample containing Hb $A_{1c}$ and at least one other form of hemoglobin, an antibody specific binding partner for the Hb $A_{1c}$, the antibody specifically binding Hb $A_{1c}$ to yield a complex, the antibody not binding to the other forms of hemoglobin in the sample;
    (b) subjecting the sample, after step (a), to capillary electrophoresis utilizing a buffer to generate an electropherogram that separates the complex from the other forms of hemoglobin in the sample, the buffer comprising:
       (i) water;
       (ii) boric acid in an amount of from 50 to 150 mM;
       (iii) a borate salt in an amount of from 15 to 35 mM;
       (iv) a sodium or potassium salt where the anion is selected from the group consisting of sulfate, chloride, fluoride, iodide, and bromide ions, the amount of sodium or potassium salt being from 50 to 100 mM; and
       (v) sufficient base compound that the buffer has a pH of from 8 to 10; and
    (c) determining the quantity of Hb $A_{1c}$ from the electropherogram.

11. The method of claim 10 wherein the buffer comprises boric acid in an amount of from 75 to 125 mM.

12. The method of claim 10 wherein the borate salt is borax, and the borax is present in an amount of from 20 to 30 mM.

13. The method of claim 10 wherein the amount of sodium or potassium salt in the buffer is from 70 to 80 mM.

14. The method of claim 10 wherein the sodium or potassium salt is sodium chloride.

15. The method of claim 10 wherein the buffer comprises a sufficient base compound that the buffer has a pH of about 8.8.

16. A method for determining the Hb $A_{1c}$ content of a sample that also contains at least one other form of hemoglobin, the method comprising the steps of:
    (a) adding to a sample containing Hb $A_{1c}$ and at least one other form of hemoglobin, an antibody specific binding partner for the Hb $A_{1c}$, the antibody specifically binding Hb $A_{1c}$ to yield a complex, the antibody not binding to the other forms of hemoglobin in the sample;
    (b) subjecting the sample, after step (a), to capillary electrophoresis utilizing a buffer, to generate an electropherogram that separates the complex from the other forms of hemoglobin in the sample, the buffer comprising:
       (i) water;
       (ii) boric acid in an amount of about 75 mM;
       (iii) borax in an amount of about 25 mM;
       (iv) sodium chloride in an amount of about 75 mM; and (v) sufficient sodium hydroxide that the buffer has a pH of about 8.8; and (c) determining the quantity of Hb $A_{1c}$ from the electropherogram.

17. A method for determining the content of a first form of hemoglobin in a sample that also contains at least one other form of hemoglobin, the method comprising the steps of:

(a) adding to a sample containing a first form of hemoglobin and at least one other form of hemoglobin, a macromolecular specific binding partner for the first form of hemoglobin, the specific binding partner specifically binding the first form to yield a complex, the antibody not binding to the other forms of hemoglobin in the sample;

(b) subjecting the sample, after step (a), to capillary electrophoresis to generate an electropherogram that separates the complex from the other forms of hemoglobin in the sample; and (c) determining the content of the first form of hemoglobin in the sample by measuring light absorbance at a wavelength at which hemoglobin significantly absorbs light and at which the macromolecular specific binding partner does not substantially absorb light.

18. The method of claim 17 wherein the first form of hemoglobin is a glycosylated hemoglobin.

19. The method of claim 17 wherein the glycosylated hemoglobin is Hb $A_{1c}$.

20. The method of claim 19 wherein the macromolecular specific binding partner is an antibody specific for Hb $A_{1c}$.

21. The method of claim 17 wherein the step of capillary electrophoresis comprises utilizing a buffer, the buffer comprising:

(i) water;

(ii) boric acid in an amount of from 50 to 150 mM;

(iii) a borate salt in an amount of from 15 to 35 mM;

(iv) a sodium or potassium salt where the anion is selected from the group consisting of sulfate, chloride, fluoride, iodide, and bromide ions, the amount of sodium or potassium salt being from 50 to 100 mM; and (v) sufficient base compound that the buffer has a pH of from 8 to 10.

22. The method of claim 21 wherein the buffer comprises (i) water; (ii) boric acid in an amount of about 75 mM; (iii) borax in an amount of about 25 mM; (iv) sodium chloride in an amount of about 75 mM; and (v) sufficient sodium hydroxide that the buffer has a pH of about 8.8.

23. The method of claim 21 wherein the wavelength at which light absorbance is measured is 415 nm.

24. The method of claim 17 further comprising the steps of:

(d) adding a known quantity of an internal standard compound to the sample prior to capillary electrophoresis, the internal standard compound being separable from the hemoglobin and being detectable in the electropherogram by a signal proportional to the quantity of internal standard compound;

(e) measuring the signal produced by the internal standard compound in the electropherogram; and (f) determining the absolute concentration of the first form of hemoglobin in the sample from a standard curve of protein concentration versus the ratio of protein signal to internal standard signal.

25. The method of claim 24 wherein the internal standard compound is 2,4-dichlorobenzoic acid and wherein the measurement of the signal produced by the internal standard compound comprises determining the absorbance of the 2,4-dichlorobenzoic acid at 214 nm.

* * * * *